United States Patent [19]
Abbott

[11] Patent Number: 5,364,765
[45] Date of Patent: Nov. 15, 1994

[54] METHOD AND REAGENT SYSTEM FOR ASSAYING ISOENZYME PROFILES

[76] Inventor: William A. Abbott, 881 Emerald Ave., Gurnee, Ill. 60031

[21] Appl. No.: 917,929

[22] Filed: Jul. 21, 1992

Related U.S. Application Data

[63] Continuation of Ser. No. 794,825, Nov. 18, 1991, abandoned, which is a continuation of Ser. No. 364,400, Jun. 9, 1989, abandoned, which is a continuation-in-part of Ser. No. 55,107, May 28, 1987, abandoned.

[51] Int. Cl.$^5$ .................. C12Q 1/52; C12Q 1/50; C12Q 1/42; C12Q 1/32
[52] U.S. Cl. .................. 435/26; 435/16; 435/17; 435/21
[58] Field of Search .................. 435/16, 17, 21, 26

[56] References Cited

U.S. PATENT DOCUMENTS

| | | | |
|---|---|---|---|
| 4,250,255 | 2/1981 | Sanford | 435/26 |
| 4,258,131 | 3/1981 | Takagahara et al. | 435/26 |
| 4,311,791 | 1/1982 | Bernstein | 435/26 |

FOREIGN PATENT DOCUMENTS

| | | | |
|---|---|---|---|
| 0352547 | 1/1990 | European Pat. Off. | 435/26 |
| 9001067 | 2/1990 | WIPO | 435/26 |

OTHER PUBLICATIONS

Merck Index (1983) 10th Ed., p. 768, Refs. 5172–5174, Merck & Co., Rahway, N.J.
Wilkinson (1976) in "The Principles and Practice of Diagnostic Enzymology", pp. 46–54, Year Book Medical Publishers, Chicago.

*Primary Examiner*—Douglas W. Robinson
*Assistant Examiner*—Jon P. Weber

[57] ABSTRACT

The present invention discloses a rapid assay method for quantitatively determining the complete isoenzyme profile of a biological fluid and a multiple-assay reagent system for carrying out the method. In one preferred embodiment, a multiple-assay reagent system is disclosed for quantifying the complete isoenzyme profile of lactate dehydrogenase in blood serum, based on two measured parameters and three performed assays.

22 Claims, 7 Drawing Sheets

(– – – –) All samples would fall on this line if isoenzyme percentages were generated by simple binomial distribution of subunits.

LDH ISOENZYME DATA BASE

474 ELECTROPHORETOGRAMS FROM OTTUMWA, IOWA

METHOD AND REAGENT SYSTEM FOR ASSAYING ISOENZYME PROFILES

CROSS REFERENCE AND RELATED APPLICATION

This application is a continuation of U.S. patent application Ser. No. 07/794,825, filed Nov. 18, 1991, abandoned, which is a continuation of application Ser. No. 07/364,400, filed Jun. 9, 1989, abandoned, which is a continuation-in-part of application Ser. No. 07/055,107, filed May 28, 1987, abandoned.

TECHNICAL FIELD

This invention relates to methods and systems for determining the amount of biologically active enzyme present in a biological fluid. In particular, the invention relates to a multiple-assay reagent system and assay method for quantitatively determining the isoenzymes of lactate dehydrogenase present in the biological fluid.

BACKGROUND OF INVENTION

Isoenzymes are catalytically active proteins that can exist in multiple forms in the same species at different life stages, in different organs and in different tissues. Certain biologically active enzymes are composed of more than one polypeptide subunit which can appear in the body as a characteristic imbalanced mixture of various isoenzymes. This imbalance produces a characteristic isoenzyme profile which can be associated with a particular physiological condition.

Lactate dehydrogenase (LDH), sometimes called lactic acid dehydrogenase or L-lactate:NAD oxidoreductase, is such a biologically active enzyme. LDH is a tetrameric protein composed of four 35 kilodalton-sized subunits which appears in the human body in five isoenzyme forms. The LDH subunits are composed of two different types of polypeptide chains, commonly called "M" and "H," which can combine and form the homotetramer and heterotetramer isoenzymes, $H_4$, $H_3M$, $H_2M_2$, $HM_3$ and $M_4$. This nomenclature arises because the M-subunit is prevalent in skeletal muscle and the H-subunit is prevalent in tile heart.

The M-subunit and H-subunit containing isoenzymes originally were identified by electrophoretic separation and were conventionally referred to as LD-1, LD-2, LD-3, LD-4 and LD-5 based on their relative migration towards the anode with LD-1 being the fastest. Their corresponding subunit compositions are $H_4$, $H_3M$, $H_2M_2$, $HM_3$ and $M_4$ respectively.

As used herein, the term "LDH" refers to lactate dehydrogenase as an enzyme species composed of all its multiple isoenzymes which contribute to its total measurable enzyme (total LDH) activity and which constitute its characteristic isoenzyme profile. The term "LD" refers to an individual isoenzyme of lactate dehydrogenase as specifically identified by the numeric suffix of 1–5. For example, the homotetramer of lactate dehydrogenase composed of H-subunits is the isoenzyme conventionally called LD-1 and the heterotetramer composed of three H-subunits and one M-subunit is the isoenzyme called LD-2.

The proportional amount of each isoenzyme of LDH varies considerably between organs and tissues but is relatively constant within any given organ or tissue. This distribution gives each organ and tissue a characteristic isoenzyme profile or pattern. For example, heart and erythrocytes have high proportions of LD-1 and LD-2, liver and skeletal muscle contain predominantly LD-5, and lung, kidney and brain contain mixtures in which LD-2, LD-3 and LD-4 may predominate to varying degrees. Presence of these isoenzymes from a diseased or damaged organ or tissue in the blood can be detected by an elevation of the total normal level of serum LDH. Further characterization of the serum isoenzyme composition can aid in identifying the physiological source responsible for isoenzymes in the blood. Thus, determinations of serum LDH and its isoenzyme composition are becoming increasingly more clinically valuable in the diagnosis of a variety of pathological disease states.

The diagnosis of suspected myocardial infarction is probably the most frequent clinical application of LDH isoenzyme determinations. In these cases, an increase in the LD-1 isoenzyme relative to the other isoforms can be specific and confirmatory for myocardial damage since the heart contains the largest proportion of the LD-1 enzyme. Speed in the diagnosis of acute myocardial infarction is desirable and often necessary to save the patient's life.

Electrophoresis was the first method used to separate the LDH isoenzymes, and is still widely used to obtain complete isoenzyme profiles. This method has several disadvantages in that it requires multiple and lengthy steps, and expensive equipment. The procedure typically requires at least about one hour to complete, with much of that time dedicated to sample manipulations by a trained technician. Separations using ion exchange columns have also been developed, but also have similar disadvantages.

An alternative approach to the analysis of LDH isoenzymes has been to selectively inhibit or denature some of the isoenzymes and so quantitate the relative proportion of those isoenzymes resistant to such treatment. For example: urea, heat and high pH have been used to progressively inactivate those isoenzymes containing the most M-subunits; high substrate levels of pyruvate or lactate have been used to selectively inhibit the H-subunit; and alpha-ketobutyric acid has been used as a substrate having a specificity for the H-subunit.

In U.S. Pat. No. 4,250,255, an approach is described where the total LDH activity is first measured, and then the isoenzymes are selectively inhibited by treating the sample with an ionic amphiphile. The treated sample is then measured for enzyme activity and that measurement is subtracted from the first measurement. The difference constitutes the activity of the uninhibited isoenzyme.

However, none of the foregoing methods can quantitate the complete isoenzyme profile of lactate dehydrogenase quickly from a single sample of biological fluid without subjecting the sample to various tedious and time-consuming manipulations, such as dilutions, pretreatments and the like or to further multi-step assays. Under clinical situations requiring relatively rapid diagnosis within minutes for treatment of a pathological state, such as in an emergency room or in a delivery room, speed and minimal sample preparation is essential.

There is a long standing clinical need for a rapid assay method and assay reagent capable of determining within minutes the completed isoenzyme profile in a biological fluid suspected of containing a biologically active enzyme, such as LDH present. This invention provides for such an assay method and assay reagent system which requires substantially no sample manipulation prior to assaying and is over 10-fold faster than present electrophoretic methods.

SUMMARY OF INVENTION

The present invention involves a method for determining the complete isoenzyme profile of a sample of biological fluid suspected of containing a biologically active enzyme composed of at least two enzymatically-active subunits occurring as a mixture of isoenzymes. The complete isoenzyme profile of that sample can be quantitatively determined by the disclosed relatively rapid assay method and multiple-assay reagent system.

The method involves measuring the enzymatic activity of at least two of the fractional subunits and the enzymatic activity of one isoenzyme. This determination can be obtained from three single-step assay mixtures prepared with an assay reagent system comprising two subunit-specific assay reagents and one isoenzyme-specific assay reagent. From that information, the complete isoenzyme profile can be algebraically quantified.

With the appropriate automated instrumentation and program, the assays can be concomitantly performed and a total LDH isoenzyme evaluation completed in about 5 minutes.

The assay method comprises dividing the sample of biological fluid into at least three portions for assaying using a multiple-assay reagent system and performing separate assays on each portion.

A first assay is performed on a first portion of the biological fluid with a first assay reagent having one set of efficiencies for measuring the enzymatic activity of a selected first subunit and a selected second subunit. A first measurement of the enzymatic activity of the first subunit and the second subunit is obtained.

A second assay is similarly performed on a second portion of the biological fluid with a subunit-specific second assay reagent having a different set of efficiencies for measuring the enzymatic activity of the same selected first subunit and second subunit. Thus, a second measurement differing from the first relative measurement is obtained. For example, the first assay reagent may have a higher efficiency for the first subunit and the second assay reagent may have a higher efficiency for the second subunit.

A third assay is performed on a third portion of the biological fluid with an isoenzyme-specific third assay reagent capable of directly quantifying the enzymatic activity of a single selected isoenzyme.

The complete isoenzyme profile in the biological fluid can then be determined. The quantitative value for each of the measured subunits is determined from the resulting algebraic expression describing the efficiency for each subunit. The total enzyme activity in the biological fluid is determined from the sum of the values for the first subunit and the second subunit obtained.

The total quantitative fractional concentration of the first selected subunit is determined from the summed value of the activity of the first selected subunit and the total enzyme activity to provide a first measured parameter. The total quantitative concentration of the one selected isoenzyme is determined from the direct measurement obtained from the third assay and the total enzyme activity to provide a second parameter. Preferably, both measured parameters are expressed in terms of percent concentration, based on the total enzyme activity.

The two measured parameters are then compared to a standard for the selected enzyme to determine the matching quantitative isoenzyme profile.

The standard can comprise one or more curves generated from known probability values for each of the subunits in an isoenzyme profile and adjusted to match each of the two measured parameters. Alternatively, the standard can be derived empirically from one or more algebraic expressions quantitatively describing the isoenzyme profile in terms of each of the same two measured parameters. For matching purposes, this empirically-derived standard includes one or more curves defined by applying linear regression analyses to a body of data composed of known characteristic isoenzyme profiles. The data is then correlated quantitatively in terms of the same two measured parameters.

Several major advantages of the assay method and assay reagent system of this invention are its speed, simplicity and accuracy.

By using an appropriate commercially available automated and programmable clinical analyzer instrument, the complete LDH isoenzyme profile in a sample of human biological fluid can be completed and evaluated in only as much time as is normally needed for a conventional total LDH assay. More particularly, by using a commercial instrument which is an automated spectrophotometric diagnostic system, a complete LDH isoenzyme profile can be quantitatively determined within about 5 minutes. The speed of the present assay method is thus over ten-fold faster than that of the well known electrophoretic methods. A major benefit is that the total LDH activity and direct LD-1 activity rapidly obtained by practicing the method and the assay reagent system of this invention provides for rapid evaluation of clinical cases presenting as potential acute myocardial infarction.

An advantage in assaying human blood serum by the present assay method is that substantially no sample manipulation is required prior to assay, apart from serum separation and aliquoting portions of sample into the sample cups of a clinical analyzer instrument. Further, the results are delivered in the same units as the total LDH and refer to undiluted serum. Where the instrument has "on-board" computing capability, total LDH, and all its individual five isoenzymes can be reported as either a percent of the total or in International Units per Liter (IU/l). In this case, no additional calculations are needed.

Moreover, the present method avoids the variability in accuracy from well known sources of error normally arising during chromatographic and electrophoretic methods. These errors arise from multiple sample manipulations, sample dilutions, delayed performance of assays and sample degradations associated therewith. For example, cost considerations often require that a clinical technician hold biological samples until sufficient samples are available to fill an electrophoretic gel plate. This typically requires ten or more samples.

The present assay method, on the other hand, relies on multiple homogeneous rate assays of a single sample and the assays have been found to be acceptably precise and reliable as disclosed herein. Moreover, each assay can be concomitantly performed using minimal amounts of sample volume, the multiple assay reagent system of this invention and a single clinical instrument. Further, where that instrument has data storage and data manipulation capability, one or more standards also can be stored "onboard" in the form of algebraic expressions and curves.

Still further benefits and advantages of the present invention will become apparent to those skilled in the art from the detailed description of the invention, the examples and claims which follow.

DETAILED DESCRIPTION OF THE INVENTION

The present invention provides for the rapid measurement of the enzymatic activity of a biological fluid and for the quantitative determination of the proportional distribution in the isoenzyme profile.

Those skilled in the art will recognize that the assay method and the assay reagent system of this invention can be appropriately adapted to determine the isoenzyme profile of biologically active enzymes composed of at least two subunits (polypeptide chains) which can occur in the human body and in a biological fluid as a mixture of isoenzyme forms. The term "biological fluid" includes whole blood, blood plasma, blood serum, spinal fluid and urine.

The term "isoenzyme" refers to a molecularly distinct subtype of an enzyme species in which one or more of its constituent subunits can be enzymatically active. The term "isoenzyme profile" refers to the relative proportional distribution pattern of the various isoforms possible for isoenzymes in a biological fluid being assayed.

The term "single-step assay mixture" means that substantially no preparatory manipulation of the sample of the biological fluid prior to mixing it with assay reagent for assaying is required as disclosed herein. The term "subunit-specific assay reagent" denotes an assay reagent having a certain efficiency for measuring the fractional enzymatic activities of at least two subunits. The term "isoenzyme-specific assay reagent" denotes an assay reagent that measures the enzymatic activity of an isoenzyme with substantially complete efficiency. The term "set of efficiencies" and "efficiency" as used herein denote the ability of a substrate to measure the active enzymatic activity of at least two subunit structures that constitute the isoenzymes present in an assay mixture.

Examples of enzymes that exist in multiple forms include lactate dehydrogenase (LDH), creatine kinase, alkaline phosphatase, maleate dehydrogenase, aspartate aminotransferase and the like.

In the case of LDH, the biological organic or physiologic source of LDH present in a biological fluid, and blood serum, in particular, can be identified by evaluating its isoenzyme profile. Characteristic isoenzyme profiles are associated with heart, skeletal muscle, erythrocytes, adrenals, liver, lung, brain and like organs and tissues. The determination of the isoenzyme profile of LDH and the proportional ratios of LD-1 to LD-2 in particular, are valuable indications of myocardial infarction.

The terms "M-subunit" and "H-subunit" as used herein denote the conventionally understood fractional subunits of LDH found predominantly in human skeletal muscle and in the heart, respectively. The present assay method is particularly suitable for rapidly determining the isoenzyme profile of LDI based on two parameters, the total enzymatic activity of the fractional M-subunits and the enzymatic activity of the LD-1 isoenzyme.

For purposes of illustrating tile present assay method and assay reagent system, but not by way of limitation, the determination of the isoenzymes of LDH in blood serum using certain LDH assay reagents will be described.

The assay method requires substantially no sample manipulation prior to the assay, apart from serum separation and allquoting into the sample cups of a clinical analyzer instrument. Assays can be performed within several minutes of preparing the assay mixture. The results are provided in the same units as LDH total and refer to undiluted serum. No additional calculations are required. Also, because no sample manipulation is required, such as dilution prior to assay, the present assay method maintains a relatively high degree of precision and accuracy.

For example, immunologic and chromatographic methods respectively require about 200 and 1000 microliters of serum sample, all of which is consumed in the assay. The present assay method requires a maximum of about 100 microliters for a manual assay, assuming that a cuvette size of 3 milliliters (ml) is used. Typically only about 0.25 to about 0.5 ml of assay reagent is required for an automated assay. An automated assay may require that about 50 to about 100 microliters of sample be in the sample cup, but the unused sample is available for other assays. Moreover, minimal dilution of the assay reagent occurs when the biological fluid is mixed with the assay reagent in preparing an assay mixture. For example, an assay mixture comprises about 1:100 parts of biological fluid sample:assay reagent.

For example, typically 10 to 20 microliters of serum per ml of assay reagent are admixed at 37 degrees C. for assaying with a clinical analyzer which uses about 2.5 to about 5.0 microliters of serum and about 0.25 ml of assay reagent, such that a greater linearity range for serum LDH and LD-1 activities ranging from 10 to 1200 IU/l can be accurately determined.

The entire assay procedure requires only as much time as is needed to perform a typical LDH total assay; e.g., about 4 to 5 minutes, with an automated spectrophotometric clinical analyzer in kinetic mode employing bichromatic filters at 340/380 nanometers (nm) or detectors measuring light absorbance at about 330 to about 380 nm. Suitable analyzers include tile Abbott VP® bichromatic batch analyzer and the Abbott SPECTRUM® Diagnostic System (Abbott Laboratories, North Chicago, Ill.).

LDH assays are generally based upon the general reaction indicated below:

$$\text{lactate} + \text{NAD} \xrightleftharpoons{\text{LDH}} \text{pyruvate} + \text{NADH} + \text{H}^+$$

in which lactate is converted to pyruvate by the enzyme with concomitant reduction of NAD (nicotinamide-adenine dinucleotide) to NADH (reduced NAD). The rate of NADH formation, or oxidation to NAD in the case of the reverse action, as measured by the rate of absorbance change at about 340 nm, is thus directly proportional to LDH activity in the sample.

One aspect of this present assay method is that the complete isoenzyme profile of LDH in a sample of biological fluid suspected of containing LDH can be quantitated within about 5 minutes by measuring two parameters using a multiple-assay LDH reagent system comprising at least three assay reagents, a single sample and a single instrument clinical analyzer. The percent H-subunit or percent M-subunit is quantified as one parameter and the percent of one LDH enzyme is quantified as the second parameter. Two of the assay reagents are subunit specific but have different sets of efficiencies for each subunit. The quantitative value of each subunit can be determined from the algebraic expression describing these efficiencies of each reagent for each subunit. By simultaneous solution of the resulting equations, the additive enzyme activities of the subunits provide total LDH activity on which percent is determined.

The remaining LDH isoenzymes can be accurately and quantitatively obtained from this information using polynomial algebraic expressions adjusted to describe the isoenzyme profile. The isoenzyme profile is matched to curves defined by applying linear regression analyses to a body of data and plotted in terms of each of the two measured parameters.

The precision and accuracy of the present assay method has been found to have acceptable linearity based on mathematical integrations of the information obtained in the assays of human blood serum as described in more detail below.

For LDH assays, the substrate of each assay reagent can be selected from the group consisting of alpha-hydroxyaliphatic acids having about 3 to 4 carbon atoms in the aliphatic chain and oxidized analogs thereof, nicotinamide-adenine dinucleotide in reduced (NADH) or oxidized (NAD) form, and substrate analogs thereof. Preferred substrates are butyrate, lactate and pyruvate.

Each assay also includes sufficient buffer to provide a pH of from about 7 to about 10. In a preferred LDH assay reagent system, each assay reagent monitors the reduction of NAD to NADH which is coupled to the oxidation of an L-2-hydroxy aliphatic acid having 3-4 carbon atoms in the aliphatic chain.

For determining the quantitative LDH isoenzyme in blood serum, a butyrate substrate is preferred for one subunit-specific assay reagent and a lactate substrate is preferred for the other subunit-specific assay reagent. For this purpose, the concentration of the substrate is preferably optimized for the H-subunit in the first assay reagent and for the M-subunit in the second assay reagent as described in detail below. Preferably, the LD-1 isoenzyme is directly measured by the third LDH assay reagent.

In a particularly preferred LDH assay reagent system of this invention, each reagent monitors the reduction of NAD. Each assay reagent, therefore, comprises substrate, NAD, and sufficient buffer to provide a pH of from about 7 to about 10, preferably from about 8 to 9.5 and more preferably from about 8.5 to about 9.

The present assay method preferably incorporates in the third LD-1 isoenzyme specific assay step, a LDH assay reagent which includes a chaotropic agent capable of selectively inactivating the isoenzymes containing one or more M-subunits, LD-2 through LD-5, and so remove their measurable enzymatic activity. As used herein, the term "chaotropic agent" refers to an inorganic anion which has a large radius, a single negative charge, and a low charge density capable of altering the second and tertiary structure of proteins.

Such chaotropic anions are members of the Hofmeister or lyotropic series. They include anions with large partial molal ionic volumes, which are designated by the symbol "phi" and expressed in units of milliliters per Mole (ml/mole). Particularly preferred anions are those with volumes greater than 30 ml/mole. Examples of such chaotropic anions are $TcO_4^-$, $ClO_4^-$, $ReO_4^-$, $BF_4^-$, $SeCN^-$, $SO_3F^-$, $SCN^-$, and $I^-$. A description of these anions is found in Wolff, J. and Maurey, J. R., *Biochim. Biophys. Acta*, 69, 58–67 (1963), the pertinent disclosures of which are incorporated herein by reference.

The foregoing chaotropic-agent containing assay reagent also contains a sufficient amount of substrate necessary for the simultaneous determination of the remaining isoenzyme composed solely of H-subunits, LD-1. The quantitation of LD-1 as well as total LDH is especially desirable and of value for diagnosing myocardial infarction, and in differentiating this disease from those involving LDH leakage from other organs. A particularly preferred assay reagent comprising L-lactate as substrate, and sodium perchlorate as the chaotropic agent is described in European Patent (E.P.) Application No. 292,838 discussed below.

The fundamental principle of that preferred third assay reagent lies in the ability of the chaotropic agent to selectively disrupt the normal structural relationships of certain proteins as they exist in aqueous solution.

Generally, a useful amount of chaotropic agent is present at a concentration of about 100 to about 5000 milliMoles/liter (mM/l), preferably at about 600 to about 1500 mM/l more preferably from about 500 to about 1000 mM/l. The presence of chaotropic agent in the assay mixture produces an immediate inactivation of all the LDH isoenzymes containing one or more M-subunits, namely, LD-2 through LD-5, in the biological fluid. LD-1 remains stable and its enzymatic activity can be measured directly by the LDH assay reagent.

In addition to inactivating the isoenzymes LD-2 through LD-5, the chaotropic agent reduces the affinity of LD-1 for substrates like lactate, pyruvate and their analogs. As a result, higher lactate concentrations are required in the presence of a chaotropic agent than in its absence to obtain equal reaction rates with the same amount of LD-1 (all else being equal, and the reaction direction being lactate→pyruvate). By the same token, the inhibitions produced by pyruvate, oxalate and high levels of lactate are also diminished. Thus, an assay reagent which is isoenzyme specific for LD-1 and contains higher levels of substrate (i.e. lactate or pyruvate) will obtain greater linearity, due to a higher concentration of available substrate throughout the reaction time frame, and a lower level of product inhibition arising during the same time frame. An additional benefit of this phenomenon is the loss of interference in samples collected in anticoagulant tubes containing oxalate salts.

Sodium perchlorate for example can reduce the affinity between the substrate (lactate or pyruvate) and the LD-1. The resulting decrease in reaction rate can be reversed by the addition of more substrate. For example, a particularly preferred LDH assay reagent comprises sodium perchlorate at about 600 mM/l to about 1000 mM/l based on perchlorate ion concentration, L-lactate substrate at about 50 mM/l to about 500 mM/l based on L-lactic acid concentration, and provides a fast and accurate direct determination of LD-1 in the presence of NAD.

Typically, LDH assay reagents include at least one substrate (typically butyrate, lactate, pyruvate, NAD, NADH or substrate analogs thereof), a buffer and optionally chromogens or indicator dyes. In some assays, NAD can be the chromogen. Additionally, assay reagents can include inhibitors, stabilizers and preservatives where needed. Basic formulae of LDH assay reagents are well known in the art and therefore, are not discussed in detail here.

Commercially available LDH assay reagents which are comprised of substrates and buffers which can be employed with the present assay method include A-GENT® LDH-L (Abbott Laboratories), LIQUID-STAT® LD-L-VV (Beckman), FAST CHEM® LDH-L (BMC), LDH-L-S V.R. (Calbiochem), C-ZYME® LDH (Coulter), COLORIMETRIX® (Dow Chemical), LDH-L (Fisher), ULTRAZYME® (Harleco), HMA LDH-VV (Hycel), SPIN CHEM® LDH-L (SKI), and LDH (L-P) (Worthington).

A preferred LDH assay reagent system comprises at least three assay reagents where the efficiency of the substrate in the first assay reagent is different from that in the second assay reagent for obtaining two different sets of measurements for the H-subunit and M-subunit.

For example, a preferred substrate for the first LDH assay reagent is a butyrate and a preferred substrate for the second LDH assay reagent is a lactate. Particularly preferred substrates include L-2-hydroxybutyric acid, 2-oxobutyric acid, and L-lactic acid. A useful first LDH assay reagent comprises a butyrate substrate based on an L-2-hydroxybutyric acid content at a concentration of about 20 to about 500 mM/l, preferably about 50 to about 300 mM/l, more preferably about 100 mM/l.

A useful second LDH assay reagent comprises an L-lactate substrate based on L-lactic acid content, at a concentration of about 100 mM/l to about 1000 mM/l, preferably about 200 mM/l to about 600 mM/l, more preferably about 400 mM/l.

Each foregoing LDH assay reagent also includes NAD at a concentration of about 2 to about 20 mM/l, preferably about 3 to about 12 mM/l, more preferably about 7 mM/l, and sufficient buffer to provide a pH of from about 7 to about 10, preferably from about 8 to about 9.5, more preferably from about 8.5 to about 9. Suitable buffers are well known in the art and include tris(hydroxymethyl) aminomethane (TRIS), L-glutamic acid (glutamate), 2-amino-2-methyl-1,3-propanediol (AMPD) and the like. A combination of TRIS and glutamate buffers is particularly preferred.

A useful assay reagent system, therefore, can comprise a kit of at least three LDH assay reagents, each supplied in separate containers. Each assay reagent can be in the form of a liquid. Preferably, stabilizers and preservatives are included in addition to substrates and buffer. Suitable stabilizers include metal-ion chelating agents, such as ethylenediaminetetracetic acid, and salts thereof. Suitable preservatives include antibiotics, such as Gentamycin sulfate, sodium azide, boric acid and the like.

Alternatively, at least one of the assay reagents can be supplied in powder form or in lyophilized form to be reconstituted for use with a diluent. In such an embodiment, the diluent can be comprised solely of water containing a portion of the constituents of the assay reagent.

In one preferred aspect, a standard is empirically derived for LDH. The complete LDH isoenzyme profile can be determined mathematically by one or more algebraic expressions in terms of the two measured parameters. Preferably an algebraic expression is used to describe the isoenzyme profile as discussed in Example 10. The isoenzyme profile is matched to curves defined by applying linear regression analyses to a body of data composed of known characteristic LDH isoenzyme profiles obtained from electrophoretograms of blood serum. The disease state associated with the isoenzyme profile can be used to diagnose the physiological sources of LDH. For matching, the curves are plotted in terms of the two measured parameters. Preferably, a computerized linear polynomial regression analyses model is used to fit the data. Those skilled in the art will recognize that other data-fitting programs and mathematical models can be used.

The standard generated for comparison of the assay results obtained by the present assay method is preferably stored "onboard" the analyzer instrument where such storage capability is available. For example, the standard can be in the form of either algrebraic equations or curves, or both, adjusted for each of the measured parameters and stored in an automated clinical analyzer. Alternatively, the standard can be maintained in any storage means from which it can be readily compared. Example storage means include a disc memory of a computer, a handheld calculator having sufficient programming and storage capacity or an analog readout means, such as a dialable selector wheel or slidable selector chart where the expected value can be read from an appropriate readout window or slot.

In a preferred embodiment, the body of data is composed of the measured characteristic complete isoenzyme profiles of a population of samples of like biological fluid known to contain the selected enzyme. The physiological disease state associated with each sample of the biological fluid containing the enzyme in the population is also known. Thus, the characteristic enzyme profile associated with certain physiological diseases or sources of the enzyme can be determined.

In one preferred embodiment of the method, the complete isoenzyme profile of lactate dehydrogenase (LDH) is quantitatively determined, preferably using blood serum. Aside from separating the serum from whole blood, no further manipulation of the sample prior to assaying is required. For LDH assays, the selected first subunit is the H-subunit of LDH, the selected second subunit is the M-subunit of LDH and the identified selected isoenzyme is the homotetramer composed of H-subunits, LD-1. The LD-1 assay reagent preferably includes a chaotropic agent capable of inactivating the measurable enzymatic activity of the other non-selected isoenzymes.

The enzymatic activity of the two LDH subunits and the LD-1 is preferably obtained by spectrophotometric means, such as an automated clinical multi-test analyzer. Preferably, an empirically derived standard is used. A useful empirical standard comprises one or more algebraic expressions adjusted for quantitatively describing the isoenzyme profile in terms of LD-1 and the M-subunit. For matching purposes, curves are generated by using linear regression analyses on a body of data composed of LDH electrophoretograms of blood serum associated with known disease states. Thus, the organic or physiological source of LDH contributing to the pathological state can be diagnosed rapidly for appropriate treatment.

A preferred multi-assay reagent system according to this invention comprises three LDH assay reagents suitable for use in the present assay method for the purpose of quantitatively determining the complete LDH isoenzyme profile in human blood serum. The first LDH assay reagent comprises at least one substrate capable of quantifying the relative difference in the enzymatic activity of the H-subunit and the M-subunit so that a first relative measurement is obtained when the reagent is mixed with a first portion of the biological fluid.

The second LDH assay reagent similarly comprises at least one substrate also capable of quantifying the relative difference in the enzymatic activity of the H-subunit and M-subunit when the reagent is mixed with a second portion of the biological fluid. However, the substrate specificity of the second assay reagent is selected to differ sufficiently from the substrate specificity of the first assay reagent to provide a second relative measurement which differs from the first relative measurement.

Preferably, the substrate concentrations of the first and second LDH assay reagents are optimized so as to maximize the difference in the efficiency of each subunit. For this purpose, optimization can be based on the difference in the enzymatic activity of the homotetramers, LD-1 and LD-5. For example, the first LDH assay reagent is optimized for the enzymatic activity of the $H_4$ subunits minus $M_4$ subunits, and the second LDH assay reagent is optimized to the enzymatic activity of the $M_4$ subunits minus the $H_4$ subunits. The total LDH enzyme activity can then be determined from the sum of the combined measurements for H-subunits and M-subunits by simultaneous solution.

In one preferred aspect for quantitatively determining LDH in blood serum, the third assay reagent of the present assay reagent system is the LD-1 specific assay reagent described in our co-assigned, co-pending application, Ser. No. 55,107, and related E.P. Application No. 292,838, the disclosures of which are incorporated herein by reference. That LD-1 specific assay reagent includes a chaotropic agent which simultaneously inactivates the enzymatic activity of the other non-selected isoenzymes while the activity of the LD-1 remains stable. The substrate concentrations are optimized so that the LD-1 activity directly measured by this reagent is equivalent to that which would be obtained using an assay reagent capable of measuring total LDH and the same amount of the "pure" LD-1.

In a particularly preferred LDH assay reagent system for assaying human blood serum by the assay method of this invention, the first assay reagent comprises a butyrate substrate, the second assay reagent comprises a lactate substrate, and the third assay reagent comprises a lactate substrate and a chaotropic agent, and each assay reagent further includes NAD and sufficient buffer to provide a pH of from about 8 to about 9.5. Preferably, the chaotropic agent in the third assay reagent is sodium perchlorate.

GLOSSARY OF MATERIALS USED

Unless otherwise noted, the following listing identifies the materials used in Examples 1–10 and FIGS. 1–7.

Substrates

1. L-lactate concentration was based on the active L-lactic acid content in a stock solution of its sodium salt.
2. L-2-Hydroxybutyrate concentration was based on the active L-2 hydroxybutyric acid content in a stock solution of a sodium salt of DL-2-hydroxybutyric acid.
3. NAD refers to the oxidized form of nicotinamide-adenine dinucleotide, $NAD^+$.

Buffers

4. TRIS refers to commercially available buffer solution of Tris(hydroxymethyl) aminomethane, also known as amino-2-(hydroxymethyl)-1,3-propanediol, at pH about 7–8.
5. Glutamate refers to L-glutamic acid buffer solution, pH about 8–9.

Chaotropic Agent

6. Active perchlorate chaotropic anion content is obtained from sodium perchlorate.

Stabilizer

7. A metal-ion chelating agent capable of blocking the generation of free radicals is preferred, such as ethylenediaminetetracetic acid, disodium salt.

Preservative

8. An antibiotic-type preservative is preferred, such as Gentamycin sulfate.

Enzyme

9. Human LD-1 (blood cells) and human LD-5 (placenta) used for optimization studies were obtained from Sigma Chemical Company (St. Louis, Mo.).

The subject invention is further illustrated by the following examples which are not intended to be limiting.

EXAMPLES 1–5

These examples illustrate compositions of LDH assay reagents suitable for use in the method of this invention. The compositions are particularly useful where the desired pH is from about 8 to about 9.5, preferably from about 8.5 to about 9, so as to monitor the reduction of NAD.

| Ingredient | Millimoles (mM) Per Liter* | | | | |
|---|---|---|---|---|---|
| | (1) | (2) | (3) | (4) | (5) |
| a) L-2-hydroxybutyrate | 100 | 200 | — | — | — |
| b) L-lactate | — | — | 400 | 87 | 200 |
| c) NAD | 7 | 7 | 7 | 7 | 7 |
| d) TRIS | 120 | 120 | 120 | 120 | 120 |
| e) Glutamate | 13 | 13 | 13 | 13 | 13 |
| f) Chaotropic Agent | — | — | — | — | 800 |
| g) Stabilizer | Q.S.** | Q.S. | Q.S. | Q.S. | Q.S. |
| h) Preservative | Q.S. | Q.S. | Q.S. | Q.S. | Q.S. |

*based on activity of substrate or chaotropic anion
**Q.S. indicates a sufficient quantity The compositions of Examples 1-5 can be freshly prepared in liquid form. Alternatively, a portion of the composition can be prepared in powder form to be dispersed in a diluent solution for use. For a powder embodiment, a sufficient amount of a substantially inert bulking agent, such as sodium chloride, can be included in the powder to provide a convenient and useful weight of powder, along with sufficient stabilizer for extending tile useful life of tile NAD when the liquid reagent is made up.

In another embodiment, part of tile substrate can be included in a powder portion with the remaining part included in the liquid portion to provide a two-part assay reagent kit that is mixed together to form the LDH assay reagent.

With regard to using the LDH assay reagents illustrated in the multiple-assay reagent system of this invention, the composition of Example 1 is particularly preferred as a first LDH assay reagent having a butyrate substrate specificity optimized for the H-subunit of LDH relative to the M-subunit. The composition of Example 3 is particularly preferred as a second LDH assay reagent having a lactate substrate specificity optimized for the M-subunit of LDH relative to the H-subunit. The composition of Example 5 is particularly preferred for use as the third LD-1 specific assay reagent.

EXAMPLE 6

This example illustrates a two-part LD-1 specific assay reagent comprised of a powder portion and diluent portion suitable for use as an LD-1 specific assay reagent in the assay method of this invention. The following powder portion was prepared specifically for reconstitution with 30 milliliters (ml) of diluent portion per gram of powder yield the following concentrations of each active component:

| Ingredient | mM/Liter of the Reconstituted Reagent |
|---|---|
| Powder Portion | |
| L-lactate | 47 |
| NAD | 7 |
| TRIS | 120 |
| Glutamate acid | 13 |
| Stabilizer | Q.S. |
| Bulking Agent | Q.S. |
| Diluent Portion | |
| L-lactate | 165 |
| Perchlorate | 825 |
| Sodium hydroxide to about pH 9 | Q.S. |
| Water | Q.S. |

Alternatively, for use as a non/enzyme specific total LDH assay reagent, the above powder portion can be reconstituted by dissolving 1.0 gram of the above powder per 30 ml of water, rather than the above diluent portion.

When the reconstituted LD-1 specific assay reagent was used with the same assay configuration, samples and instruments as for a total LDH assay reagent, the resulting enzymatic activity measured was that due only to the LD-1 isoenzyme. Moreover, the LD-1 activity units were directly proportional to those which would be measured if the same amount of pure LD-1 were assayed by a total LDH reagent, for example by reconstituting the powder portion with water instead of the diluent.

Other LD-1 specific assay reagents can be prepared from commercially existing powder or liquid total LDH assay reagents. The exact formulae for the diluent portion can be arrived at by optimization studies, carried out as follows. A population of human serum samples, including those with elevated LDH and LD-1, are obtained and the LD-1 levels determined by established immunologic, electrophoretic or chromatographic methods for LD-1 determination (i.e., the reference method). The data are correlated with those obtained by reconstituting an existing LDH reagent powder with various diluent solutions containing different concentrations of L-lactate and/or sodium perchlorate (i.e., the experimental conditions).

The sodium perchlorate may range in perchlorate anion concentration from about 100 to about 5000 mM/l, preferably from 500 to about 1500 mM/l, more preferably from 600 to about 1000 mM/l and the L-lactate can vary from about zero to about 500 mM/l. The results of the. LD-1 reference method are then compared to each experimental condition using linear regression analyses to obtain values for the slope, intercept and correlation coefficient for each comparison. An optimized LD-1 reagent can be derived from such analyses by the selection of the diluent formulation which yields a slope and correlation coefficient each approaching unity, and an intercept value approaching zero, The above procedure allows a preexisting powdered or lyophilized reagent formulation for total LDH to be easily adapted for the selective assay of the LD-1 isoenzyme. The results obtained from one human sample from both the total LDH and LD-1 assays can be readily combined to arrive at an LD-1 :LDH ratio, which has been shown to be of diagnostic value.

EXAMPLE 7

This example demonstrates the excellent correlation between results obtained with the LD-1 specific assay reagent of Example 6 from a single-step assay mixture to that of a multi-step standard procedure for the isolation of serum LD-1.

The single-step assay mixture comprised mixing the serum sample with the LD-1 specific assay reagent of Example 6 with no prior preparation of the sample, according to the one-step method described in E.P. Application No. 292,838. Duplicate aliquot samples were assayed directly on the Abbott VP ® bichromatic batch analyzer and on the Abbott SPECTRUM ® diagnostic system clinical analyzer, each set in kinetic mode, using Abbott A-GENT ®, LDH reagent, which contains substrate, NAD, and buffers but no chaotropic agent. Approximately 250 microliters of assay reagent were employed to assay 2.5 microliters of sample on the Abbott VP ® and 5 microliters of sample on the Abbott SPECTRUM ® instruments.

For comparison, the serum samples were pre-treated following the commercial ISOMUNE-LD ® procedure of Roche Diagnostic Systems (Nutley, N.J.). The ISOMUNE-LD procedure and assay for isolating LD-1 was performed as follows. To the aliquots of sample were added Anti-LD-5 ($M_4$) Serum (goat), mixed and incubated for 5 minutes at ambient room temperature. Next a second antibody suspension (donkey) was added to the aliquots, mixed and incubated for an additional 5 minutes at ambient temperature and then centrifuged. Duplicate 5 and 10 microliters samples of the supernatants were then assayed as above to determine LD-1 isoenzyme activity with conventional reagent, in this case Abbott's A-GENT ® LDH Reagent.

A computerized program for linear regression analysis was used to determine the correlation of the two procedures on each clinical apparatus and the results were graphed. The graphs appear in FIG. 1 for the assay conducted on the Abbott VP ® analyzer and in FIG. 2 for the assays conducted on the Abbott SPECTRUM ® analyzer. The LD-1 assay results obtained with the LD-1 specific assay reagent of Example 6 were plotted on the Y axis while the multi-step standard assay results were plotted on the X axis. A perfect correlation would bisect the graph with a zero intercept and 1.0 slope. The correlation results were as follows:

|  | ABBOTT VP ® Standard* versus LD-1 Reagent** | ABBOTT SPECTRUM ® Standard* versus LD-1 Reagent** |
| --- | --- | --- |
| Intercept | −0.041 | 0.445 |
| Slope | 1.01 | 0.947 |
| Correlation | 0.997 | 0.994 |
| Number of samples | 102 | 92 |

*multi-step method LD-1 assay performed with ISOMUNE-LD ® reagent to isolate LD-1 and then determined with A-GENT ® LDH reagent
**one-step method with the LD-1 specific assay reagent of Example 6.

The results showed substantially excellent correlation between the multi-step procedure which involved first isolating LD-1 from the serum sample and then measuring LD-1 activity and the LD-1 specific reagent in a one-step method which simultaneously isolated and measured the LD-1 activity. Thus, the one-step method of preparing an assay mixture, and the LD-1 specific assay reagent were found particularly preferred for the present assay method.

EXAMPLE 8

This example illustrates the optimization of an LDH assay reagent to maximize the difference in the efficiency of the enzymatic activity of the H-subunit ($H_4$) relative to that of the M-subunit ($M_4$). The exact formula of an optimized first LDH assay reagent can be then selected.

The composition of an LDH assay reagent corresponding to that of Example 1 was prepared, except that the concentration of the L-2-hydroxybutyrate substrate was varied from 20 to about 100 mM/l. The difference in the efficiency of the activity of the fractional H-subunit and M-subunit was determined using LD-1 and LD-5. Otherwise, the procedure for preparing the assay mixture, the sample volume size and the VP$^R$ bichromatic batch analyzer described in Example 7 was used.

For comparison, the efficiency of the data was graphed relative to the percent efficiency of the enzyme activity determined with an assay reagent comprising L-lactate substrate at L-lactic acid concentration of 70 mM/l. From the graphed data shown in FIG. 3 for the $H_4$ (shown by the squares) and the data for the $M_4$ (shown by the cross marks), the maximum difference in efficiency of the reagent for the H-subunits minus the M-subunits ($H_4 - M_4$) was determined to be optimized at a butyrate concentration of about 100 mM/l as shown by the dotted line. At the optimized substrate concentration, the efficiency of the LDH assay reagent was judged to be about 69.6 percent for the H-subunit and about 20.7 percent for the M-subunit. The optimized assay reagent was judged suitable as an H-subunit specific "first" LDH assay reagent of this invention.

EXAMPLE 9

The procedure for Example 8 was followed, except that the composition of the LDH assay reagent corresponding to that of Example 3 was prepared and the lactate substrate was varied from about 100 mM/l to about 500 mM/l.

Figure 4:
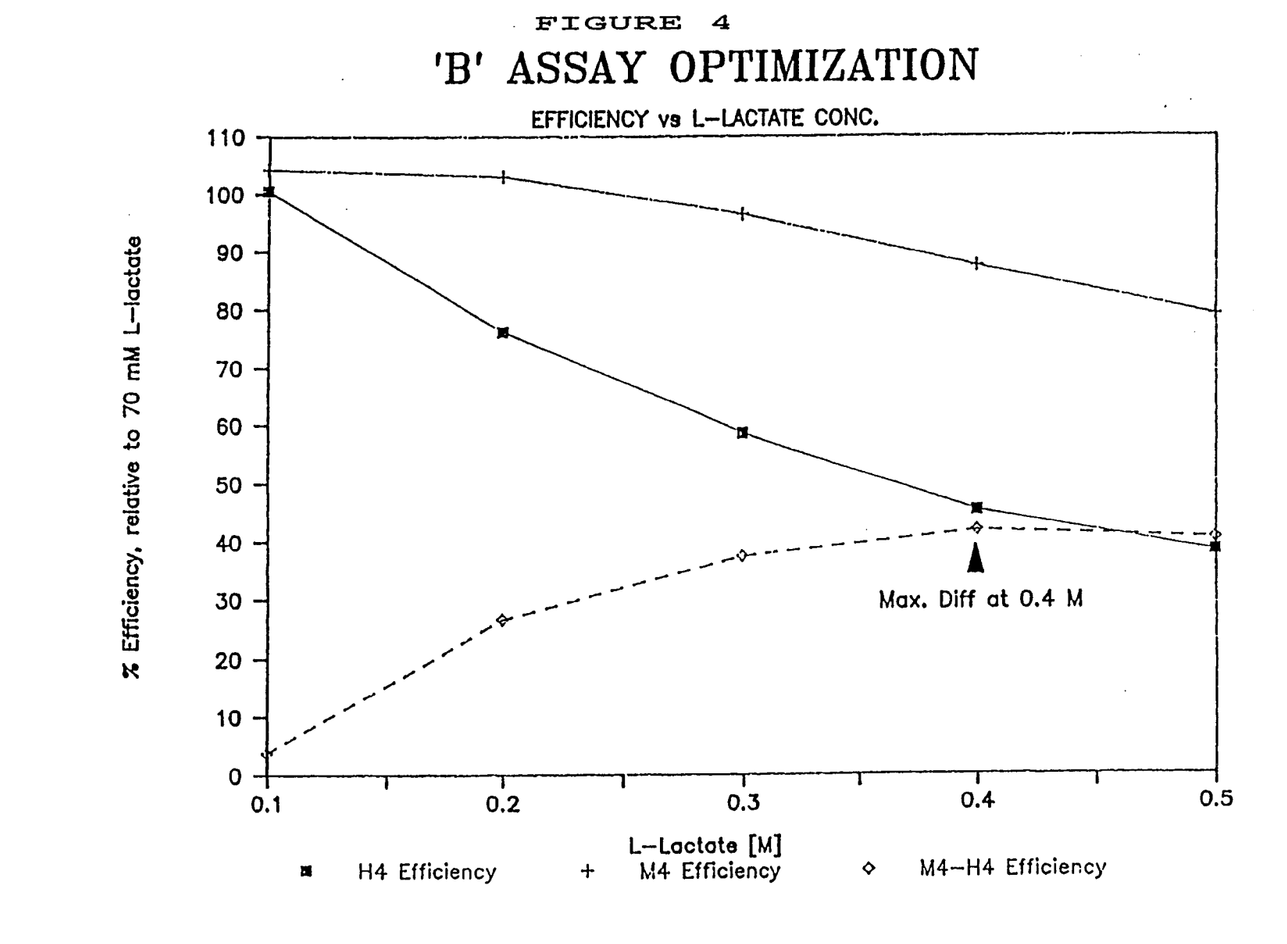
FIG. 4 graphically shows the optimization of another LDH assay reagent as in FIG. 3 comprising L-lactate substrate at various concentrations.

From the graphed data shown in FIG. 4, the maximum difference in enzymatic efficiency of the reagent for the M-subunits minus the H-subunits ($M_4 - H_4$) was optimized at an L-lactate concentration of about 400 mM/l. The efficiency of this optimized LDH assay reagent was judged to be about 45.4 for the H-subunits and about 95.2 percent for the M-subunits.

The optimized assay reagent was judged suitable as an M-subunit specific "second" LDH assay reagent for a multiple-assay reagent system where the first LDH assay reagent was optimized as in Example 8.

EXAMPLE 10

This example illustrates the generation of an empirical standard for LDH derived from a body of data composed of known isoenzyme profiles and an LDH assay reagent system. The example also illustrates the appropriateness of selecting the fractional enzymatic activity of the M-subunit and the LD-1 isoenzyme as the two measured parameters from which the activities of the remaining LDH isoenzymes can be mathematically determined.

Samples of blood serum were obtained from the Ottumwa Regional Health Foundation in Ottumwa, Iowa. The samples represented a relatively large patient group of at least 85 patients. The samples represented one or more sequential samplings per patient, with a maximum of ten samplings from any one individual. Electrophoretograms were made to generate a body of data having a wide range of known LDH isoenzymes profile values from serum associated with a wide variety of pathological states. A commercial band-type electrophoresis kit (Beckman PARAGON-LD) was used according to the manufacturer's instructions.

Assuming that LDH isoenzyme variability can be predicted based on the quantitation of one fractional subunit composition and one isoenzyme, one set of data representing 85 electrophoretograms was subjected to linear polynomial regressional analysis in two variables. A set of data points was obtained utilizing the well-known method of least squares, also known as the root mean square (RMS) error, in the following equation (1):

$$D = A_1 + A_2X + A_3X^2 + A_4Y + A_5Y^2 + A_6XY + A_7X^2Y + A_8XY^2 + A_9X^2Y^2 \quad (1)$$

where
- D = dependent variable,
- X,Y = independent variables, and
- $A_1$–$A_9$ = coefficients of independent variables The percent M-subunit was used as the independent variable "X" and the percent of each isoenzyme was evaluated as either the independent variable "Y" or the dependent variable "D".

The coefficients ($A_1$–$A_9$) for each isoenzyme were obtained by using a commercially available computer program written for Polynomial Regression in Two Variables for use with a personal computer (APPLE II model). The output of the program printed the nine equation coefficients followed by the RMS errors of the estimate. From this output, the values of the dependent variable D for any given value of X and Y could be predicted.

The RMS errors of the regression analyses for the 85 electrophoretograms are tabulated below.

| Y VARIABLE | LD-1 | LD-2 | LD-3 | LD-4 | LD-5 | SUM |
|---|---|---|---|---|---|---|
| LD-1 | — | 2.21 | 2.69 | 1.76 | 1.81 | 8.47 |
| LD-2 | 2.33 | — | 3.69 | 2.34 | 3.26 | 11.62 |
| LD-3 | 8.36 | 4.29 | — | 1.55 | 1.34 | 15.54 |
| LD-4 | 4.59 | 4.97 | 3.21 | — | 2.40 | 15.17 |
| LD-5 | 3.27 | 3.82 | 1.53 | 1.18 | — | 8.90 |

The data show LD-1 isoenzyme provided the closest fit for the other isoenzymes based on the summed minimum value of the RMS errors, i.e. 8.47.

The isoenzyme profiles for a second set of data representing from 474 electrophoretograms were algebraically determined as follows. The total percent M-subunits [X=0.25 (percent LD-2)+0.5 (percent LD-3)+0.75 (percent LD-4)+LD-5] and percent LD-1 (Y) in each sample were used as independent variables to predict the percent of LD-2, LD-3, LD-4 and LD-5 (each a dependent variable D) in equation (1). The coefficients ($A_1$–$A_9$) for each isoenzyme were again obtained by the method of least squares. The resulting equations were judged to accurately describe the isoenzyme profile.

The RMS errors of the fit for the coefficients (calculated D values) and the data range for percent LD-2, LD-3, LD-4 and LD-5 isoenzyme based on total LDH obtained for the 474 electrophoretograms were as follows:

| Isoenzyme | LD-2 | LD-3 | LD-4 | LD-5 | SUM |
|---|---|---|---|---|---|
|  | 2.03 | 2.72 | 1.41 | 1.49 | 7.65 |
| Percent Range | 11–53 | 6–33 | 1–23 | 0–68 |  |

As shown by the data, the summed value of the RMS errors decreased to a minimum of 7.65 when the body of electrophoretic data was increased from 85 to 474.

The regression analyses of the above pooled predicted versus real data values is shown below for the fit of the 474 individual observed data points per isoenzyme and the combined 1896 data points.

| REGRESSION ANALYSES OF EACH ISOENZYME FIT, AND COMBINED FIT | | | | | |
|---|---|---|---|---|---|
|  | LD-2 | LD-3 | LD-4 | LD-5 | COMBINED |
| Intercept | 3.88 | 5.14 | 1.78 | 0.22 | 0.34 |
| Standard Error of Y intercept | 1.93 | 2.31 | 1.20 | 1.47 | 1.97 |
| Slope | 0.90 | 0.72 | 0.72 | 0.98 | 0.98 |
| Standard Error of Slope | 0.01 | 0.02 | 0.02 | 0.01 | 0.00 |
| Correlation Coefficient | 0.95 | 0.85 | 0.85 | 0.99 | 0.99 |
| Number (n) of observations | 474 | 474 | 474 | 474 | 1896 |

Thus the regression analyses showed that the predicted value=0.98 (real)+0.34 percent; where the correlation coefficient of the real data=0.99 for n=1896. Correlation was judged acceptable.

The results showed that the complete LDH isoenzyme profile was quantitatively determinable by comparing two measured parameters, the fractional M-subunit and the LD-1 in terms of percent of total LDH.

Figure 5:
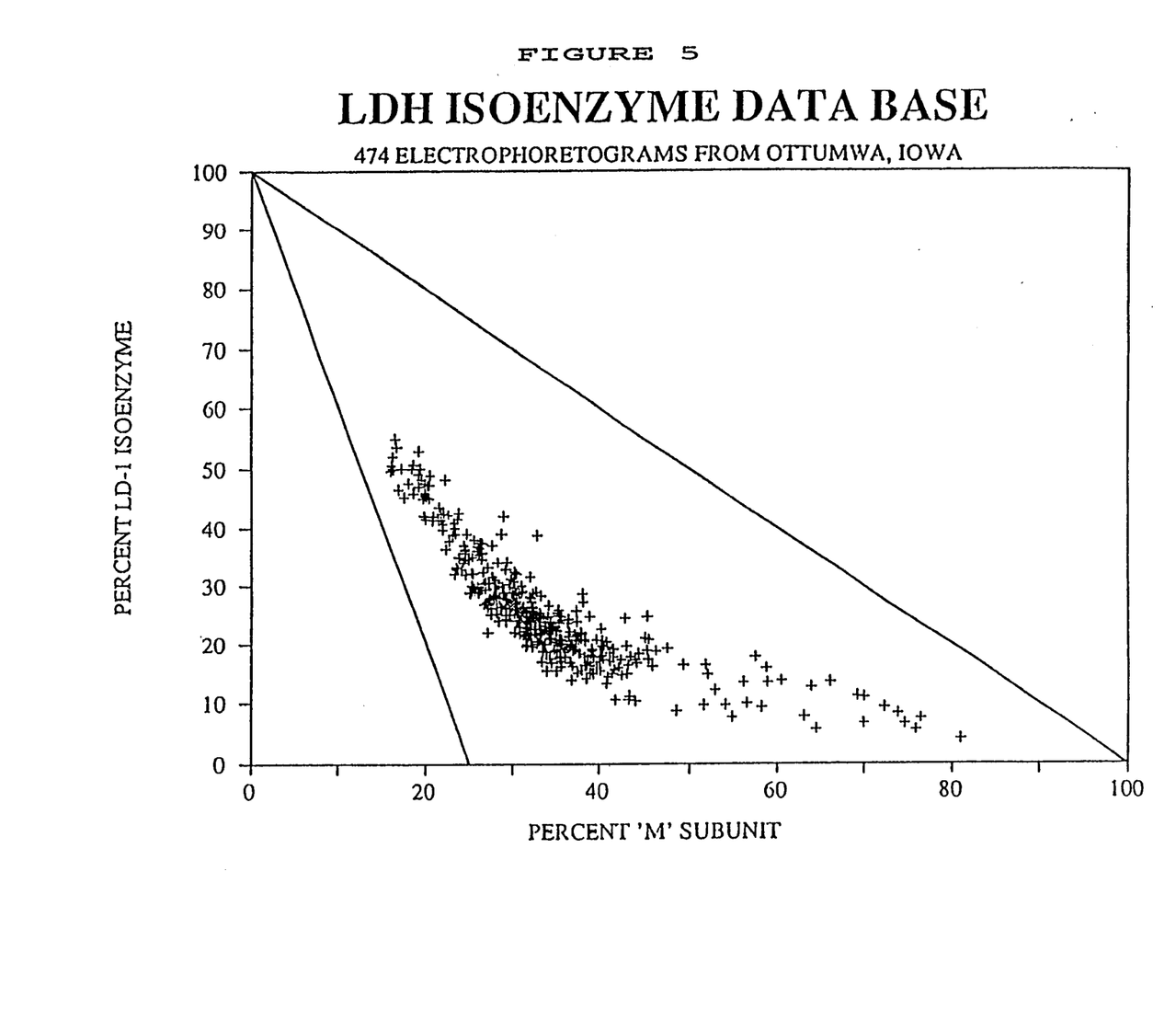
FIG. 5 graphically shows a body of data for LDH isoenzyme profile generated from a population of 474 electrophoretograms of blood serum obtained from humans having various pathological conditions where the data are plotted in terms of percent M-subunit and percent LD-1 enzyme activity.

FIG. 5 graphically shows a plot of the LDH isoenzyme database generated from the information obtained from the actual 474 electrophoretograms in terms of percent M-subunit and percent LD-1 isoenzyme. The data include the cumulative information from the above 85 electrophoretograms and 389 additional electrophoretograms.

Figure 6:
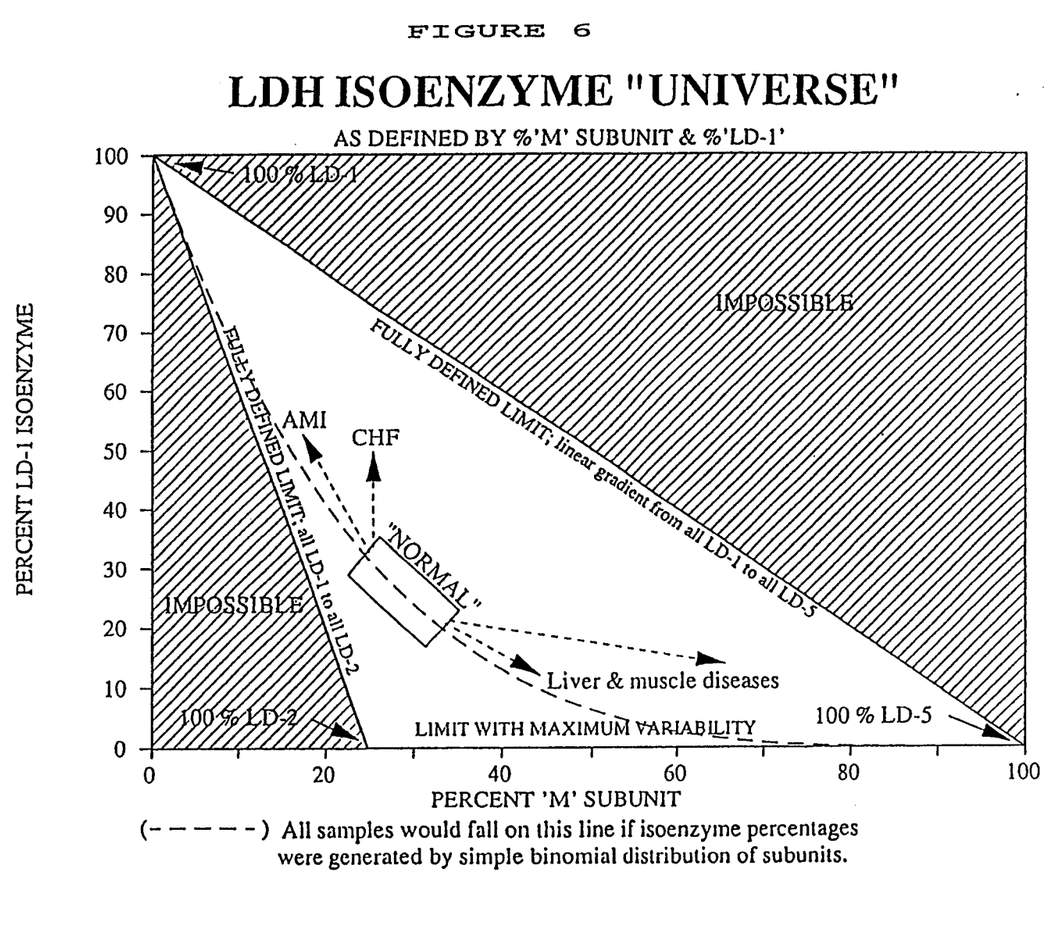
FIG. 6 graphically illustrates an LDH isoenzyme universe defined by the same two parameters of FIG. 5 in which disease states having known isoenzyme profiles occur.

For comparison, FIG. 6 graphically illustrates an LDH isoenzyme universe also defined by percent M-subunit and percent LD-1 isoenzyme. The universe comprises the fully defined limits for the linear gradient from all LD-1 to all LD-5 variations, the fully defined limit for all LD-1 to all LD-2 variations, and the limit with maximum variability of percent M-subunits. As further seen in FIG. 6 if isoenzyme percentages were generated by simple binomial distribution of subunits, all samples would fall on the dotted line. Normal values for LDH isoenzyme profile are represented by the boxed area, and specific variations in the enzyme profile from the norm can be determined for various pathologic states, such as acute myocardial infarction (AMF), congestive heart failure (CHF), liver or muscle diseases and the like.

Figure 7:
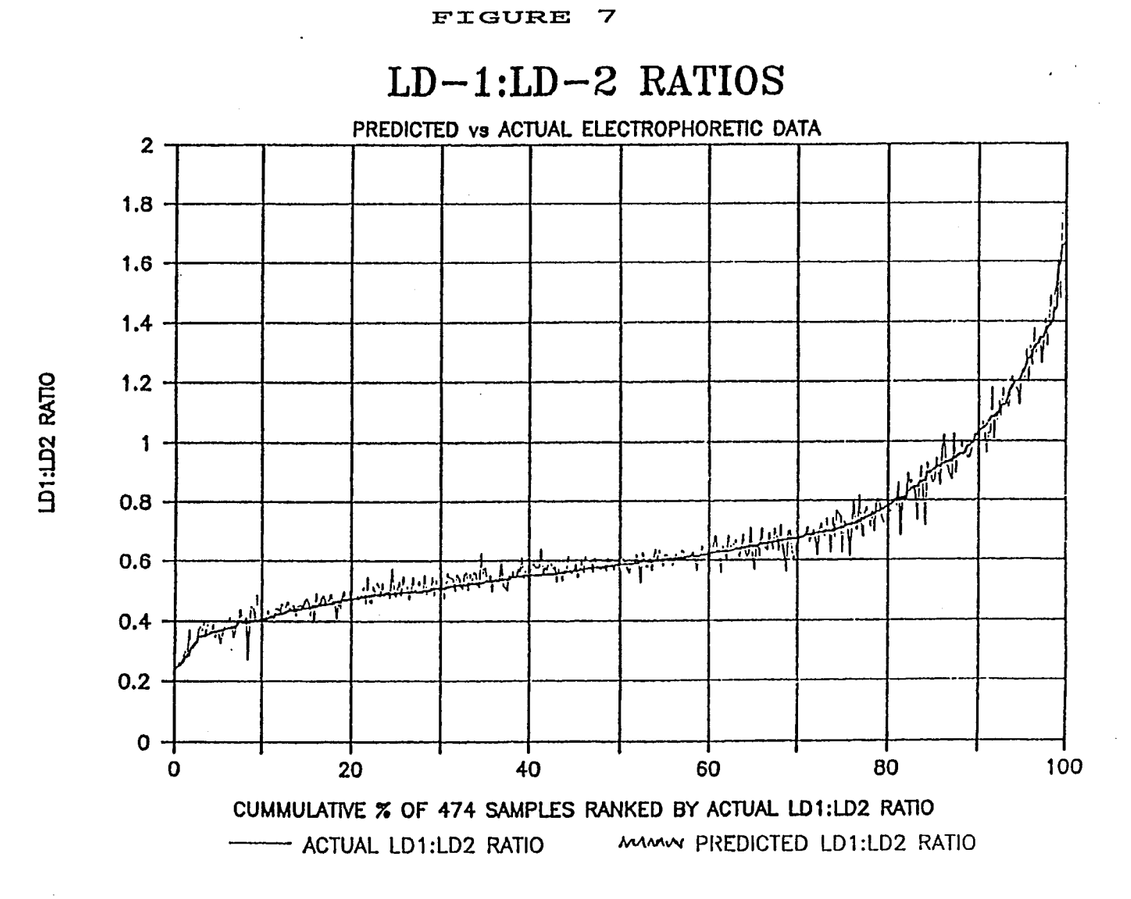
FIG. 7 graphically compares the predicted ratios of LD-1:LD-2 isoenzymes to actual ratios of LD-1:LD-2 ranked from the cumulative percentage information of the population of samples of FIG. 5.

Additionally, FIG. 7 graphically illustrates the ranked ratio of LD-1:LD-2 for the actual and predicted electrophoretic data, shown by the solid and wavy lines, respectively, from the cumulative percent values of the 474 electrophoretograms of blood serum.

Based on the good correlation obtained with the above mathematical model, the two parameters, percent M-subunit and percent LD-1 isoenzyme were adopted for the LDH assay method of this invention. These findings also showed the appropriateness of using the two parameters for blood serum to predict isoenzyme profiles and are generally in agreement with the findings of other researchers.

For example, Feldman recently concluded that serum LDH isoenzyme patterns could be reduced to the fraction of M-subunit ($P_m$) and the distribution of that subunit among the five isoenzymes. See Feldman, "The $P_m$ Distribution: A Model For Interpreting LD Isoenzyme Patterns," Clin. Chem. Acta, 135, 109–134 (1983), the relevant portions of which are incorporated herein by reference. Unlike Feldman's proposed model, however, the present assay method provides for directly inferring the complete LDH isoenzyme profile from two parameters: i.e., the fraction of M-subunits and the total LD-1, both of which are determined by direct homogeneous rate reactions.

Figure 1:
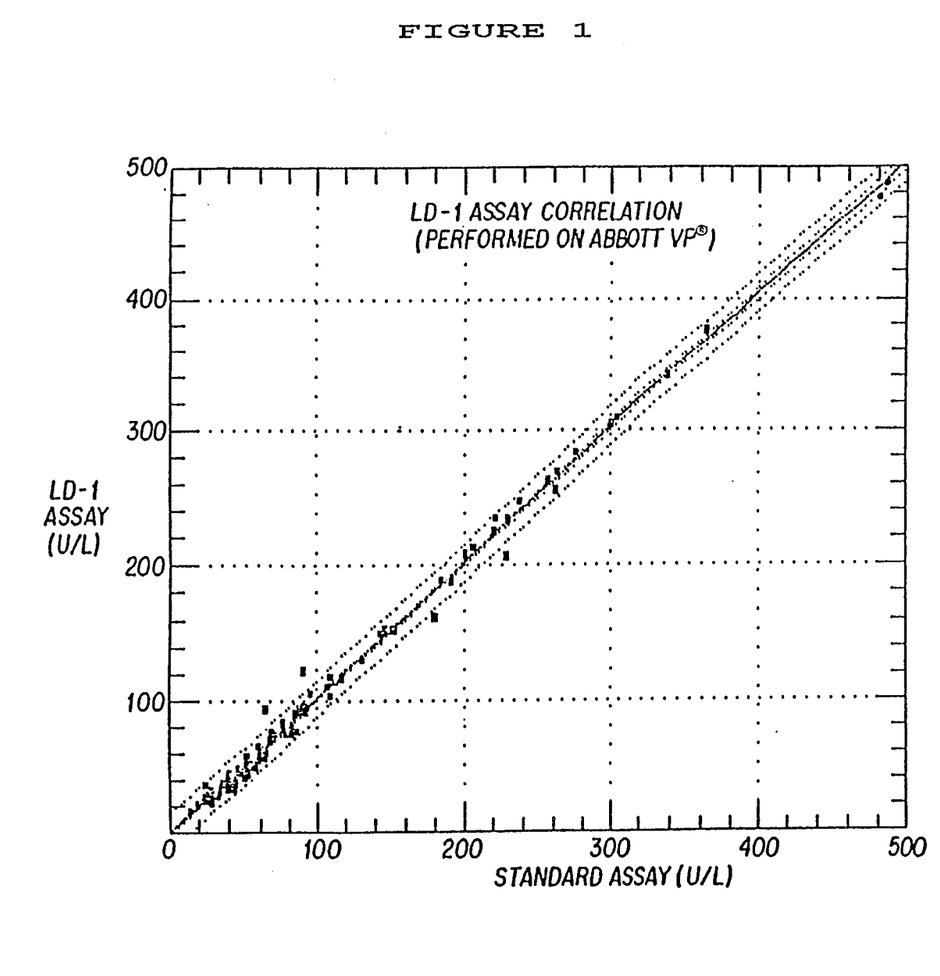
FIG. 1 shows LD-1 assay results performed by an LD-1 specific assay reagent suitable for use in the assay method of this invention where the results are obtained with single-step assay mixtures and are correlated to results obtained with a multi-step standard method using an Abbott VP ® bichromatic batch analyzer.
Figure 2:
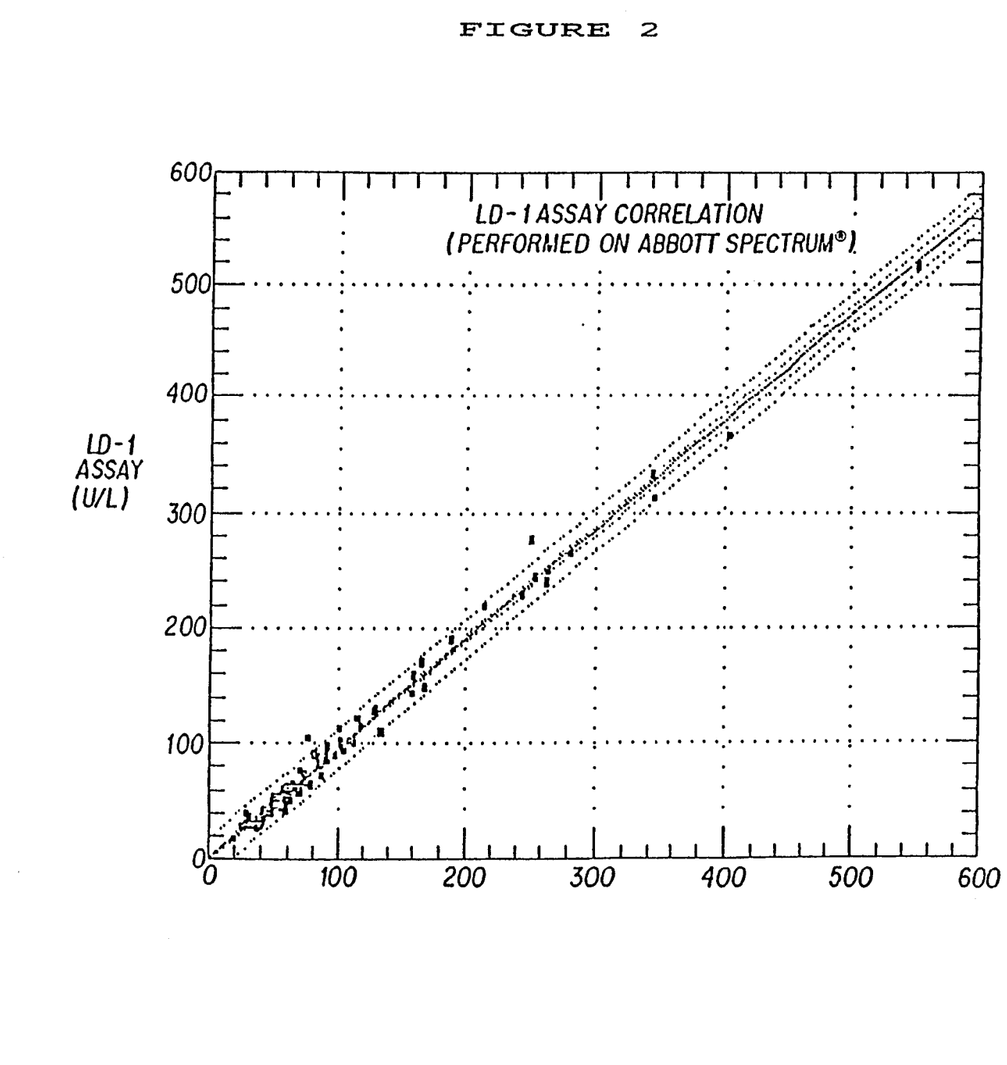
FIG. 2 shows another correlation of the results of the LD-1 assay and the multi-step standard method of FIG. 1 using the Abbott SPECTRUM ® diagnostic system analyzer.
Figure 3:
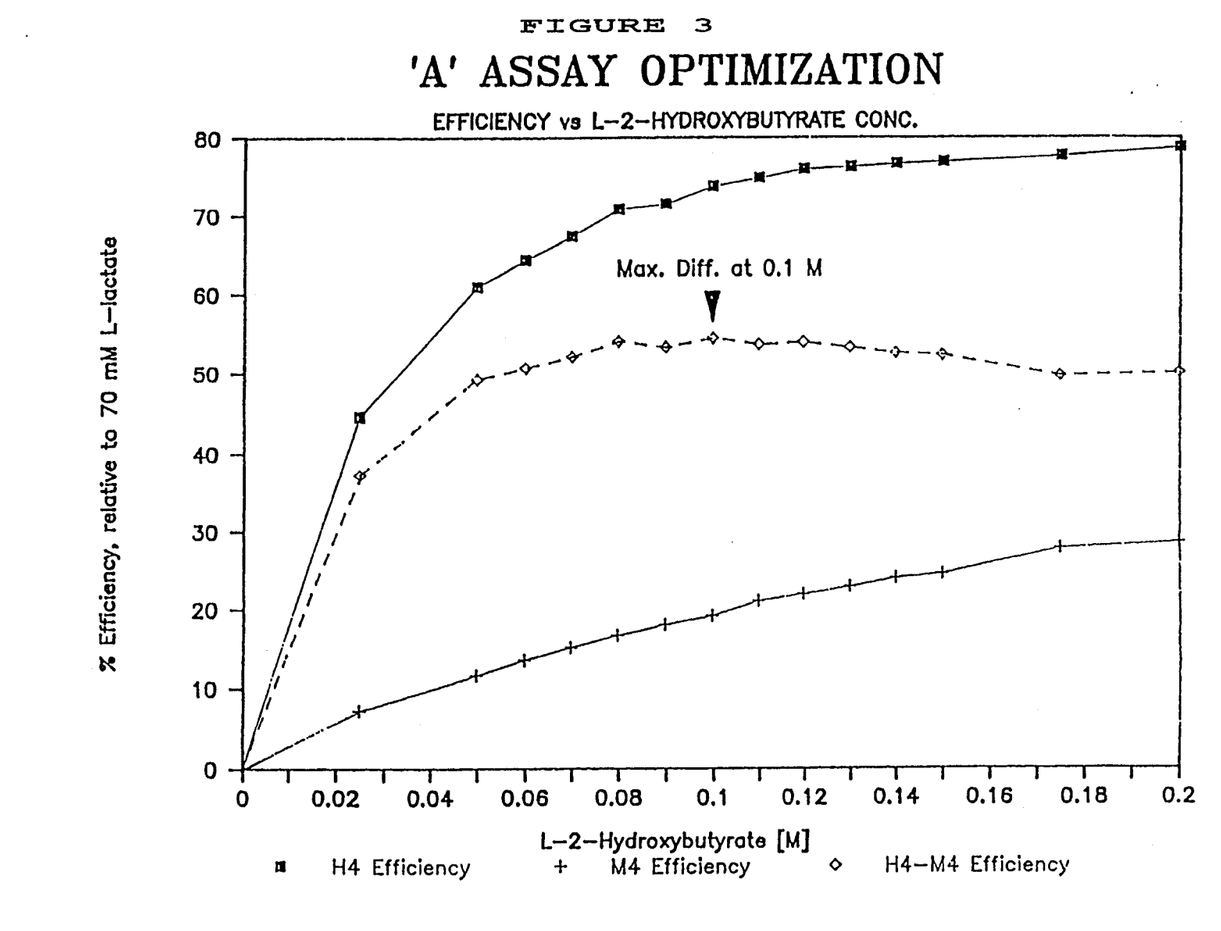
FIG. 3 graphically shows the optimization of an LDH assay reagent comprising L-2 hydroxybutyrate substrate at various concentrations relative to the efficiency of an assay reagent having L-lactate substrate at a single concentration.

FIGS. 3 and 4 discussed in Examples 8 and 9 respectively, each illustrate one preferred approach for selecting a first and second assay reagent by optimizing the substrate specificity of each assay reagent so as to maximize the difference in the efficiency of each subunit. For this purpose, the homotetramer composed of H-subunits, $H_4$, namely LD-1 isoenzyme, and the homotetramer composed of M-subunits, $M_4$, namely LD-5 isoenzyme, were used. The appropriateness of using these homotetramers for interpolating the relative affinities of the three remaining heterotetramers, namely the LD-2, LD-3 and LD-4 isoenzymes, has been confirmed by other researchers. See Gubierna et al., "Estimation of Correlation of Lactate Dehydrogenase Subunits Mole Quota Based on Differences in Substrate Inhibition," *Molec. Cellul. Biochem.*, 19, 165–170 (1978), the pertinent disclosures of which are incorporated herein by reference.

In a preferred method for assaying LDH in blood serum, the multiple-assay reagent system comprises first and second assay reagents which are each subunit-specific. The assays can be based on the same or different substrates, as long as each assay reagent has differing sets of efficiencies to obtain different measurements from which total LDH activity can be determined. For this purpose, each subunit specific assay reagent can be optimized as described earlier in Examples 8 and 9. The LD-1 isoenzyme is preferably determined directly with the LD-1 specific reagent described in Example 7. Thus, the reduction of NAD+ to NADH, preferably at pH of from about 8 to about 9.5, can be monitored by all three assay reagents as a system.

The rate of NADH formed can be measured spectrophotometrically by the rate of absorbance increase at 340 nm, preferably by using an Abbott SPECTRUM ® diagnostic system which is a random access multi-test analyzer. With such an instrument, each assay can be performed by the method of this invention concomitantly.

The total enzyme activity, LDH, in blood serum can then be obtained by combining the measurements obtained with the optimized first assay reagent and the second optimized assay reagent. For example, from the information on sets of efficiencies obtained for the optimized LDH assay reagent of Example 8 containing 100 mM/l L-2-hydroxybutyrate as substrate, 7 mM/l NAD+ and sufficient glutamate buffer at pH about 8.8 (identified as assay reagent A); and the optimized LDH reagents of Example 9 containing 400 mM/l L-lactate, 7mM/l NAD and sufficient glutamate buffer at about pH 8.8 (identified as assay reagent B), the following algebraic equations (2) and (3) can be written.

$$A = 0.696(H) + 0.207(M) \quad (2)$$

$$B = 0.454(H) + 0.952(M) \quad (3)$$

The total LDH enzyme activity, which is the sum of the value of the H-subunits and M-subunits, can be obtained by the simultaneous solution of equations (2) and (3) as written in equation (4).

$$M + H = 0.8751(A) + 0.8609(B) = \text{Total LDH activity.} \quad (4)$$

The fractional M-subunit activity and percent M-subunit activity, respectively, can be determined according to the following equations (5) and (6).

$$\text{M-subunit activity} = -0.797(A) + 1.224(B) \quad (5)$$

$$\text{Percent M-subunits} = \text{M-subunit/total LDH times } 100. \quad (6)$$

This percent value is the "X" parameter in the polynomial regression equation (1) where the value of the total LDH activity is obtained from equation (4).

In the present LDH assay method, the percent value for the "Y" parameter in equation (1) can be obtained by the direct measurement of LD-1 activity with a third LD-1 specific assay reagent. From this information, a relative relationship according to the following equation (7) can be written:

$$\text{percent (LD-1} = \text{LD-1 activity/total LDH activity,} \quad (7)$$

where the value for total LDH activity is obtained from equation (4).

The complete isoenzyme profile of the LDH in a given biological sample fluid, therefore, can be quantitatively described by substituting the values obtained from equations (6) and (7) in equation (1). The described isoenzyme profile can then be matched by comparing the quantitative fractional percent of the M-subunit obtained in equation (6) and the percent LD-1 obtained in equation (7) to a standard curve defined by applying regression analyses to a body of data composed of characteristic isoenzyme profiles of LDH plotted in terms of the two measured parameters.

Such a body of data can be generated from electrophoretic data from human blood serum as illustrated in this example.

The present invention has been described generally and with respect to preferred embodiments. It will be clear to those skilled in the art that modifications and variations of the disclosed methods and compositions can be made without departing from the scope of the invention.

What is claimed is:

1. An assay method for quantitatively determining the isoenzyme profile of a biologically active enzyme present in a selected biological fluid, the method comprising the steps of:
    (a) providing a sample of a biological fluid selected from the group consisting of whole blood, blood serum, blood plasma, spinal fluid and urine, said biological fluid suspected of containing an enzyme selected from the group consisting of lactate dehydrogenase, creatine kinase, alkaline phosphatase, maleate dehydrogenase and aspartate aminotransferase, which enzymes comprise at least two enzymatically active subunits and occur as a mixture of isoenzymes in the biological fluid;
    (b) dividing the biological fluid into at least three portions and;
        (i) performing a first assay on a first portion of the biological fluid with a first reagent having differential subunit efficiencies for measuring the enzymatic activity of a selected first subunit and a selected second subunit to obtain a first measurement;
        (ii) performing a second assay on a second portion of the biological fluid with a second reagent having different efficiencies than the first reagent for measuring the enzymatic activity of the selected first subunit and the selected second subunit to obtain a second measurement;

(iii) performing a third assay on a third portion of the biological fluid with an isoenzyme reagent which quantifies a single selected enzymatically active isoenzyme to obtain a direct measurement;

(c) determining the quantitative value for each of the measured subunits and the sum of the values of the subunits obtained in steps b(i) and b(ii) as a measure of the total enzyme activity in the biological fluid;

(d) determining the total quantitative fractional concentration of the first selected subunit from the summed value for that subunit and the total enzyme activity obtained in step (c) to provide a first calculated parameter;

(e) determining the total quantitative concentration of the one selected isoenzyme from the measurement obtained in step b(iii) and the total enzyme activity obtained in step (c) to provide a second calculated parameter; and (f) comparing the calculated parameters obtained in steps (d) and (e) to a standard for the selected enzyme to determine the isoenzyme profile of the enzyme present in the biological fluid.

2. The assay method of claim 1 wherein the standard comprises one or more curves generated from known probability values for each of the subunits in an isoenzyme profile adjusted to match each of the two calculated parameters.

3. The assay method of claim 1 wherein the standard is derived empirically, the empirical standard comprising one or more algebraic expressions quantitatively describing the isoenzyme profile in terms of each of the same two calculated parameters and including one or more curves generated from a body of data composed of known isoenzyme profiles for the selected enzyme.

4. The assay method of claim 1 wherein each assay reagent contains at least one substrate selected from the group consisting of alpha-hydroxyaliphatic acids having about 3 to 4 carbon atoms in the aliphatic chain and oxidized analogs thereof, nicotinamide-adenine dinucleotide in reduced or oxidized form, and substrate analogs thereof.

5. The assay method of claim 1 wherein each assay reagent further includes a buffer for providing a pH of from about 7 to about 10.

6. The assay method of claim 1 wherein the third assay comprises at least one isoenzyme-specific substrate and a chaotropic agent which inactivates the measurable enzymatic activity of all but the selected isoenzyme.

7. The assay method of claim 6 wherein the chaotropic agent is an inorganic salt having an anion that is a member of the lyotropic series selected from the group consisting of $TcO_4^-$, $ClO_4^-$, $ReO_4^-$, $BF_4^-$, $SCN^-$ and $I^-$.

8. The assay method of claim 7 wherein the chaotropic agent is sodium perchlorate.

9. The assay method of claim 1 wherein each assay reagent includes nicotinamide-adenine dinucleotide.

10. The assay method of claim 1 wherein the selected enzyme is lactate dehydrogenase, the identified first selected subunit is an H-subunit, the identified second selected subunit is an M-subunit and the identified single selected isoenzyme is a homotetramer.

11. The assay method of claim 10 wherein the first reagent comprises a butyrate substrate, the second reagent comprises a lactate substrate, and the isoenzyme reagent comprises a lactate substrate and a chaotropic agent, each assay reagent further including nicotinamide-adenine dinucleotide and sufficient buffer to provide a pH from about 7 to about 10.

12. The assay method of claim 11 wherein the chaotropic agent is sodium perchlorate.

13. The assay method of claim 11 wherein the selected isoenzyme is the H-subunit homotetramer, LD-1.

14. An assay method for quantitatively determining the complete isoenzyme profile of lactate dehydrogenase in a selected sample of blood serum comprising the steps of:

(a) dividing the sample into at least three portions and without further preparation;

(i) assaying for the enzymatic activity of the H-subunits and the M-subunits of the lactate dehydrogenase isoenzymes present in at least two of the portions using different lactate dehydrogenase reagents for each portion, each reagent having differential subunit efficiencies for measuring subunit activity to obtain two differing measurements;

(ii) assaying for the enzymatic activity of the isoenzyme composed of H-subunits, LD-1, in a third portion of the sample with a lactate dehydrogenase isoenzyme reagent capable of quantifying the LD-1 isoenzyme directly;

(b) determining the quantitative value for each of the measured subunits and the sum of the values of the H-subunits and M-subunits obtained in step a(i) as a measure of the total lactate dehydrogenase enzyme activity of the blood serum;

(c) determining the quantitative fractional enzymatic activity of the M-subunit from the summed value and total enzyme activity obtained in step (b);

(d) determining the quantitative enzymatic activity of the LD-1 from the direct measurement of the enzymatic activity of LD-1 obtained in step a(ii) and the total enzymatic activity obtained in step (b); and (e) comparing the combined enzymatic activity of the M-subunits of lactate dehydrogenase isoenzyme obtained in step (b) and the enzymatic activity of the LD-1 obtained in step (d) to a standard derived empirically, the standard comprising one or more algebraic expressions quantitatively describing the isoenzyme profile in terms of each of the same two calculated parameters and adjusted to match one or more curves defined by a body of data composed of known isoenzyme profiles of lactate dehydrogenase to determine the isoenzyme profile of the enzyme present in the blood serum.

15. The assay method of claim 14 wherein at least one of the reagents in step a(i) comprises a butyrate substrate, nicotinamide-adenine dinucleotide, and sufficient buffer to provide a pH of from about 8 to about 9.5.

16. The assay method of claim 14 wherein at least one of the reagents in step a(i) comprises a lactate substrate, nicotinamide-adenine dinucleotide, and sufficient buffer to provide a pH from about 8 to about 9.5.

17. The assay method of claim 14 wherein the isoenzyme reagent in step a(ii) comprises a lactate substrate, nicotinamide-adenine dinucleotide, a chaotropic agent, and sufficient buffer to provide a pH from about 8 to about 9.5.

18. The assay method of claim 17 wherein the chaotropic agent is an inorganic salt having an anion that is a member of the lyotropic series selected from the group consisting of $TcO_4^-$, $ClO_4^-$, $ReO_4$, $SCN^-$ and $I^-$.

19. The assay method of claim 18 wherein the chaotropic agent is sodium perchlorate.

20. The assay method of claim 14 wherein the enzymatic activities in steps a(i) and a(ii) are measured by spectrophotometric means and the data for the standard in step (e) are generated by electrophoretic means.

21. The assay method of claim 20 wherein at least one of the reagents in step a(i) comprises an alpha-hydroxyaliphatic acid having about 3 to 4 carbon atoms in the aliphatic chain or oxidized analog thereof as a substrate, and the isoenzyme reagent in step a(ii) comprises lactate as a substrate and a chaotropic agent, each assay reagent further including nicotinamide adenine-dinucleotide and sufficient buffer to provide a pH of from about 8 to about 9.5.

22. The method of claim 21 wherein one of the alpha-hydroxyaliphatic acid substrates in the reagents in step a(i) and a(ii) is a butyrate and the other is a lactate, and the chaotropic agent in the reagent in step a(ii) is sodium perchlorate.

* * * * *